United States Patent
Yamamoto

(10) Patent No.: US 7,550,290 B2
(45) Date of Patent: Jun. 23, 2009

(54) SENSOR

(75) Inventor: Tomohiro Yamamoto, Hirakata (JP)

(73) Assignee: Panasonic Corporation, Osaka (JP)

( * ) Notice: Subject to any disclaimer, the term of this patent is extended or adjusted under 35 U.S.C. 154(b) by 742 days.

(21) Appl. No.: 10/548,200

(22) PCT Filed: May 11, 2004

(86) PCT No.: PCT/JP2004/006618

§ 371 (c)(1),
(2), (4) Date: Sep. 7, 2005

(87) PCT Pub. No.: WO2004/102176

PCT Pub. Date: Nov. 25, 2004

(65) Prior Publication Data

US 2006/0099107 A1     May 11, 2006

(30) Foreign Application Priority Data

May 15, 2003    (JP)    ............... 2003-136959

(51) Int. Cl.
*G01N 27/327*    (2006.01)
(52) U.S. Cl. ............... 435/287.8; 204/400; 204/403.01; 435/288.5; 435/817; 436/806; 422/57
(58) Field of Classification Search ............ 204/403.4, 204/193, 403.06, 400; 205/777.5
See application file for complete search history.

(56) References Cited

U.S. PATENT DOCUMENTS

| | | | |
|---|---|---|---|
| 4,088,448 A | | 5/1978 | Lilja et al. |
| 4,676,274 A | * | 6/1987 | Brown .................... 137/806 |
| 5,928,880 A | * | 7/1999 | Wilding et al. ............ 435/7.21 |
| 2002/0148726 A1 | * | 10/2002 | Yamamoto et al. ..... 204/403.14 |

FOREIGN PATENT DOCUMENTS

| | | |
|---|---|---|
| JP | 07-110313 | 4/1995 |
| JP | 2001-305093 A | 10/2001 |
| JP | 2002-202283 A | 7/2002 |
| JP | 2002-340839 A | 11/2002 |
| JP | 2003-065997 A | 3/2003 |
| JP | 2003-075389 | 3/2003 |
| JP | 2003-075389 A | 3/2003 |
| WO | WO 01/84133 A1 | 11/2001 |
| WO | WO 02/054054 A1 | 7/2002 |
| WO | WO 02/095385 A1 | 11/2002 |
| WO | WO 03/074999 A1 | 9/2003 |

* cited by examiner

*Primary Examiner*—Tony G Soohoo
*Assistant Examiner*—Robert Eom
(74) *Attorney, Agent, or Firm*—McDermott Will & Emery LLP

(57) ABSTRACT

In order to realize a sensor that is capable of promptly and accurately supplying a small amount of a liquid sample to a filtration part even if the sensor is not held substantially horizontally, this invention provides a sensor having means for supplying a liquid sample to the filtration part by capillary action.

8 Claims, 5 Drawing Sheets

SENSOR

RELATED APPLICATION

This application is a national phase of PCT/JP2004/006618 filed on May 11, 2004, which claims priority from Japanese Application No. 2003-136959 filed on May 15, 2003, the disclosures of which Applications are incorporated by reference herein. The benefit of the filing and priority dates of the International and Japanese Applications is respectfully requested.

TECHNICAL FIELD

The present invention relates to a sensor for quantifying or detecting a specific component in a liquid sample.

BACKGROUND ART

Biosensors are known as sensors that detect specific components in liquid samples such as body fluids.

Biosensors refer to sensors that utilize biological materials, such as microorganisms, enzymes, antibodies, DNA, and RNA, as molecule identification elements. That is, a biosensor quantifies or detects a specific component contained in a liquid sample by utilizing a reaction that occurs when a biological material recognizes the specific component, for example, oxygen consumption by respiration of microorganisms, enzyme reaction, light emission, etc.

Among various biosensors, enzyme sensors have been extensively commercialized. For example, enzyme sensors which are sensors for glucose, lactic acid, cholesterol, amino acids and the like are utilized in medical measurements, the food industry, etc.

Such an enzyme sensor quantifies a substrate contained in a liquid sample, for example, by reducing an electron mediator by electrons that are produced by a reaction between a specific substance contained in the liquid sample and e.g., an enzyme, and electrochemically measuring the amount of the reduced electron mediator with a measuring device.

In using such a sensor that measures a specific component in a liquid sample, it may become necessary to remove substances that are essentially unnecessary for reaction, substances that can adversely affect reaction and the like from the liquid sample. For example, when a cholesterol sensor contains a surfactant in its reaction system, it may become necessary to remove hemocytes from blood which is a liquid sample. This is because hemocytes are destroyed by the surfactant so that reducing substances contained in the hemocytes, such as glutathione, may adversely affect reaction.

Specifically, it is common to employ a structure of providing a filtration part for removing hemocytes near an opening to which a liquid sample is supplied. As the structure of the filtration part, for example, three systems as illustrated in FIGS. 6 to 8 have been proposed. Therein, filtration is done with a filter provided in the filtration part.

FIG. 6 is a schematic view showing a horizontal separation system. With the system as shown in this figure, blood which is a liquid sample is dropped to the vicinity of the end (primary end) of a filter on the side where a liquid sample is supplied, and the blood is filtered in the horizontal direction. Blood plasma is caused to ooze from the end (secondary end) of the filter on the side where a filtered liquid sample oozes out (see International Publication No. WO 02/054054 A1, for example).

Also, FIG. 7 is a schematic view showing a vertical separation system. With the system as shown in this figure, blood is directly dropped to the primary end of a filter and is filtered in the vertical direction, and blood plasma is caused to ooze from the bottom face of the filter or the vicinity thereof at the secondary end.

FIG. 8 is a schematic view showing a combined separation system. With the system as shown in this figure, blood is directly dropped to the primary end of a filter and is filtered in the vertical direction and then the horizontal direction, and blood plasma is caused to ooze from the secondary end of the filter (see International Publication No. WO 02/095385 A1, for example). With any of these systems, the use of a preferable filter enables removal of hemocytes before they reach the reaction system.

However, the sensors employing these systems of FIGS. 6 to 8 involve directly dropping a liquid sample to the primary end of the filter or the vicinity thereof, and such structure causes the following problems.

First, it is difficult to adequately regulate the amount of a liquid sample to be measured and supply it to the filtration part. Thus, the amount of a liquid sample supplied to the filtration part tends to become excessive or insufficient. Second, it is difficult to continuously supply a liquid sample to the filter at an appropriate speed. Hence, it is possible that a liquid sample is not supplied at a speed commensurate with the filtration performance of the filtration part. As a result of these first and second problems, the function of the filtration part is not fully exhibited, thereby causing a decrease in measurement accuracy, a decline in within-run reproducibility, and an increase in measurement time.

Third, when dropping a liquid sample, the user needs to keep the sensor substantially horizontally. Also, when the user drops blood from his/her finger, the user must drop blood accurately to a proper drop position. That is, further improvements are necessary also in terms of user operability.

For example, International Publication No. WO 03/074999 A1 proposes a biosensor equipped with a liquid sample supply inlet in the shape of a trapezoid that is like a reverse cone; however, this proposal also cannot solve the above-mentioned third problem. Further, when the amount of a liquid sample dropped is small, there is also a problem in that this liquid sample adheres to the portion in the shape of a trapezoid like a reverse cone, not duly reaching the filtration part.

It is therefore an object of the present invention to provide a sensor that is capable of supplying a liquid sample to a filter promptly and readily even if it is not held substantially horizontally, and that is capable of supplying even a small amount of a liquid sample to the central part of the filter promptly and readily.

DISCLOSURE OF INVENTION

The present invention relates to a sensor including: a filtration part; supply means of supplying a liquid sample to the filtration part by capillary action; and a reaction part having a reagent that reacts with the liquid sample that has been filtered in the filtration part.

Preferably, the reaction part is provided on a base plate, and the supply means sucks the liquid sample in a substantially horizontal direction relative to the base plate.

The filtration part preferably filters the liquid sample supplied from the supply means in a direction substantially vertical to the base plate.

The supply means preferably has a first opening to which the liquid sample is supplied, and a second opening through which the liquid sample is supplied to the filtration part, with a space connecting the first opening with the second opening.

An air vent is preferably arranged in the supply means such that the liquid sample supplied to the first opening is sucked into the second opening.

The air vent and the first opening are preferably arranged on opposite sides of the second opening of the supply means.

Preferably, the supply means includes a first cover, spacers, and a second cover, the second opening is provided in the second cover, and the spacers form the first opening and the air vent.

The space preferably narrows from the first opening toward the second opening. Also, the space preferably narrows from the air vent toward the second opening.

The distance from the first opening to the second opening is preferably equal to or grater than the distance from the second opening to the air vent.

The largest width of the second opening is preferably equal to or greater than the smallest width of the space.

The largest width of the second opening is preferably equal to or less than the distance from the center of the second opening to the air vent.

Preferably, the filtration part includes a filter that filters the liquid sample, and the cross-sectional area of the second opening is smaller than the cross-sectional area of the filter.

The cross-section of the second opening is preferably similar to the cross-section of the filter.

The volume of the space from the first opening to the second opening is preferably equal to or larger than the total volume of the volume of a gap around the filter and the volume of a space in the reaction part.

The reaction part preferably has a second air vent.

BEST MODE FOR CARRYING OUT THE INVENTION

In order to solve the above problems, in a sensor of the present invention, a liquid sample is supplied to a filtration part by supply means having a predetermined structure and function for filtration, and the liquid sample that has been filtered at the filtration part is then supplied to a reaction part having reagents that react with the liquid sample.

Referring now to drawings, one embodiment of the present invention is hereinafter described in detail. The embodiments and respective figures of the present invention that will be described below are not to be construed as limiting particularly the present invention.

Figure 1:
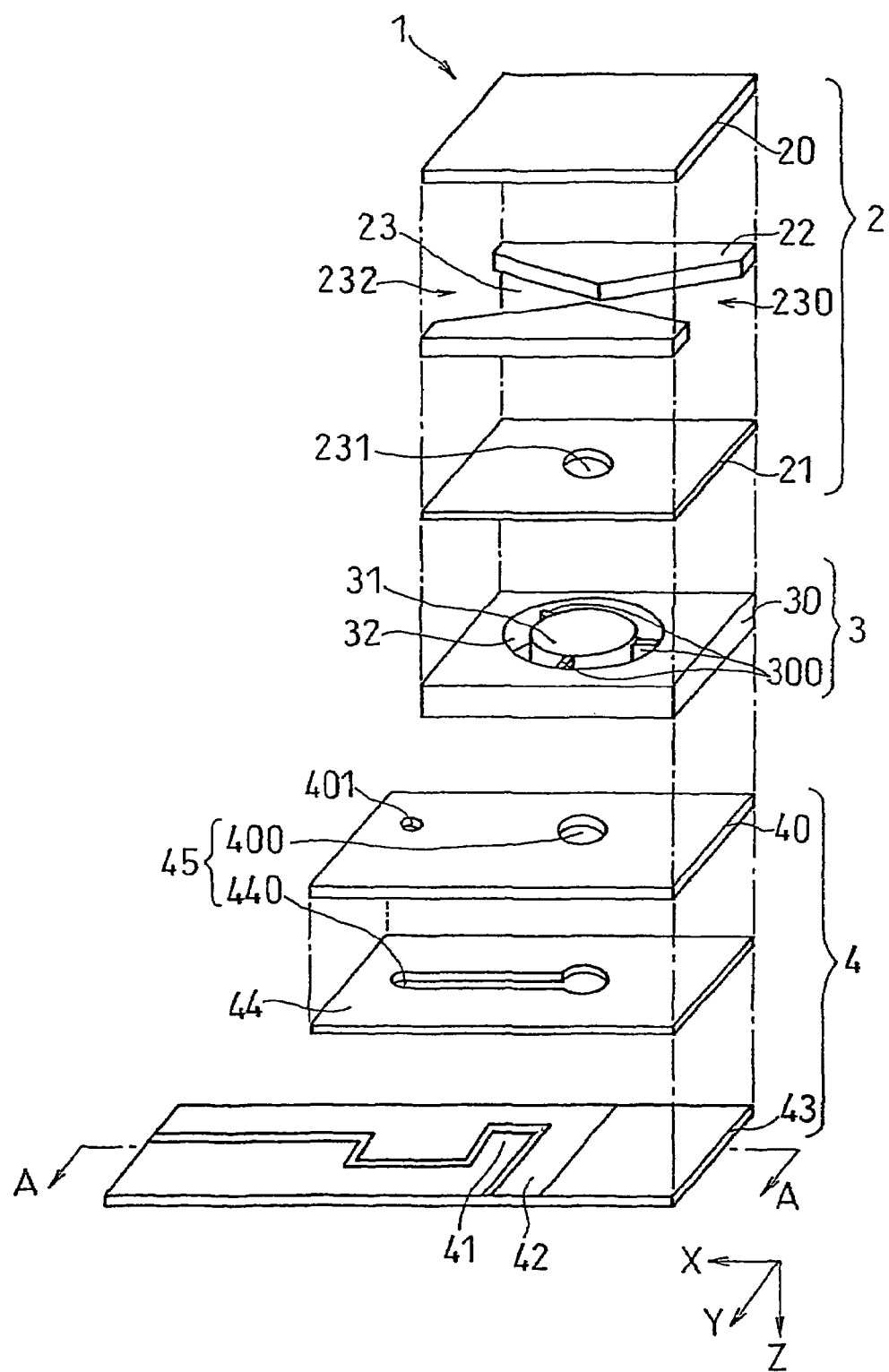
FIG. 1 is an exploded perspective view of a sensor according to one embodiment of the present invention.

Outline of the Invention:

Referring to FIG. 1, which is an exploded perspective view of a sensor 1, the outline of the sensor 1 is described prior to detailed descriptions of respective components of the sensor according to this embodiment. As illustrated in FIG. 1, the sensor 1 has supply means 2, a filtration part 3, and a reaction part 4. The sensor 1 is greatly different from conventional sensors in that the filtration part 3 is equipped with the supply means 2 for supplying a liquid sample. A liquid sample is not directly supplied to the filtration part, but is supplied to the filtration part 3 via the supply means 2.

The supply means 2 has a capillary structure, so that a liquid sample is supplied to the filtration part 3 by capillary action. As used herein, "capillary action" refers to the phenomenon in which when a narrow tube is stood in a liquid, the liquid level in the tube moves up or down relative to other horizontal levels due to the action of the adhesion of the liquid to the intra-tube surface and the surface tension thereof.

By capillary action, a liquid sample is promptly supplied to the filtration part 3. Since the amount of the liquid sample is regulated by the supply means 2, the liquid sample can be prevented from being excessively supplied to the filtration part 3. Also, since the portion of the filtration part 3 to which the liquid sample is supplied can be regulated by the positional relation between the supply means 2 and the filtration part 3, the liquid sample can be prevented from being supplied to an inadequate portion of the filtration part 3.

Accordingly, it is possible to prevent the filtration function of the filtration part 3 from degrading. Also, since the liquid sample reaching the reaction part 4 is filtered appropriately, the reaction with reagents in the reaction part 4 proceeds appropriately, thereby resulting in an improvement in the measurement accuracy and simultaneous reproducibility of the sensor 1.

Exemplary liquid samples that may be used in the sensor 1 of this embodiment include biological fluids such as blood (including either case of whole blood and a cell-free component such as blood plasma or blood serum), interstitial fluid, skin exudate, sweat, tear, and urine. Also, exemplary analytes in liquid samples that may be used include glucose, cholesterol, and lactic acid.

The sensor 1 is particularly suited for quantification of cholesterol, glucose, and lactic acid in human blood. Taking as an example the quantification of cholesterol contained in human blood, the structure of the sensor 1 is described more specifically.

Structure of Sensor:

As illustrated in FIG. 1, the sensor 1 comprises the supply means 2, the filtration part 3 and the reaction part 4 which are laminated in this order in the thickness direction of the sensor 1. The Z direction as shown in the figure is referred to as the thickness direction of the sensor 1. Also, the X direction is referred to as the length direction of the sensor 1, and the Y direction is referred to as the width direction of the sensor 1. With respect to the filtration system, the vertical separation system is employed.

The supply means 2 is composed of a first cover (capillary cover) 20, a second cover (filter cover) 21 with a second opening 231 that communicates with a filter, and two spacers (capillary spacers) 22. Between the first cover 20 and the second cover 21, the two spacers (capillary spacers) 22 form a first opening 230 serving as a sample supply inlet, an air vent 232, and a space 23 having the first opening 230 and the air vent 232.

The supply means 2 has a suitable shape such that a liquid sample supplied to the first opening 230 is sucked into the second opening 231 by capillary action, as will be described below.

The material of the first cover 20, the second cover 21 and the spacers 22 may be a material that is sufficiently rigid during storage and upon measurement. Examples include thermoplastic resins, such as polyethylene, polystyrene, polyvinyl chloride, polyamide, and saturated polyester resin, and thermosetting resins, such as urea resin, melamine resin, phenolic resin, epoxy resin, and unsaturated polyester resin.

Also, these constituent members may be composed of different members or may be composed of the same member. For example, the first cover 20, the second cover 21, and the spacers 22 may be composed of the same member, and they may be formed integrally.

The filtration part 3 is composed of a filter spacer 30 and a cylindrical filter 31 placed between the second cover 21 and a reaction part cover 40 with a filter connection hole 400 and a second air vent 401 formed therein. The filter spacer 30 has filter-holding parts 300 in the form of protrusions for directly holding the filter 31. The filter 31 is held by the filter-holding parts 300, the second cover 21, and the reaction part cover 40. While the filter 31 is held, a gap 32, which is a space around the filter 31, is formed between the second opening 231 and the connection hole 400.

The material of the filter 31 may be glass, paper, polyester non-woven fibers, etc. Also, the size of the pores of the filter 31 is designed such that hemocytes do not pass therethrough. More specifically, the pore size is designed so as to create a difference in flow resistance between blood plasma and hemocytes, to the extent that blood passes through the filter 31 in such an amount that its blood plasma fills the whole liquid sample supply path 440 that will be described below but its hemocytes do not reach the secondary end of the filter 31. The filter spacer 30 and the filter-holding parts 300 may be composed of a material that is sufficiently rigid during storage and upon measurement, in the same manner as the above-mentioned spacers 22 and the like.

The reaction part 4 is composed of the reaction part cover 40, a base plate 43, and a reaction part spacer 44. The base plate 43 is provided with a pair of electrodes (electrode system) comprising a working electrode 41 and a counter electrode 42. The reaction part spacer 44 with a cavity is interposed between the reaction part cover 40 and the base plate 43, to form the liquid sample supply path 440. That is, the liquid sample supply path 440 is a space formed by the cavity of the reaction part spacer 44 and the connection hole 400 of the reaction part cover 40.

The liquid sample supply path 440 is provided with reagents. The reagents may be provided as reagent layers on the electrode system or in the vicinity thereof. Alternatively, they may be mixed with a conductive material that forms the working electrode 41 and the counter electrode 42, so as to be contained in the electrodes. When a reagent layer is provided on the electrode system, it is preferable to form a hydrophilic polymer layer so as to come in contact with the reagent layer, in order to suppress separation of the reagent layer. This embodiment employs the structure of providing a reagent layer on the electrode system, as will be described below.

The base plate 43, the reaction part spacer 44, and the reaction part cover 40 are formed of an insulating material, such as polyethylene terephthalate. Examples include thermoplastic resins, such as polyethylene, polystyrene, polyvinyl chloride, polyamide, and saturated polyester resin, and thermosetting resins, such as urea resin, melamine resin, phenolic resin, epoxy resin, and unsaturated polyester resin.

The working electrode 41 and the counter electrode 42 are formed by sputtering a conductive material, such as palladium, on the surface of the base plate 43 and then trimming it with a laser. This pattern and the cavity of the reaction part spacer 44 define the areas of the electrodes. The working electrode 41 and the counter electrode 42 may be composed of a commonly used conductive material, such as palladium, gold, platinum, or carbon.

Figure 2:
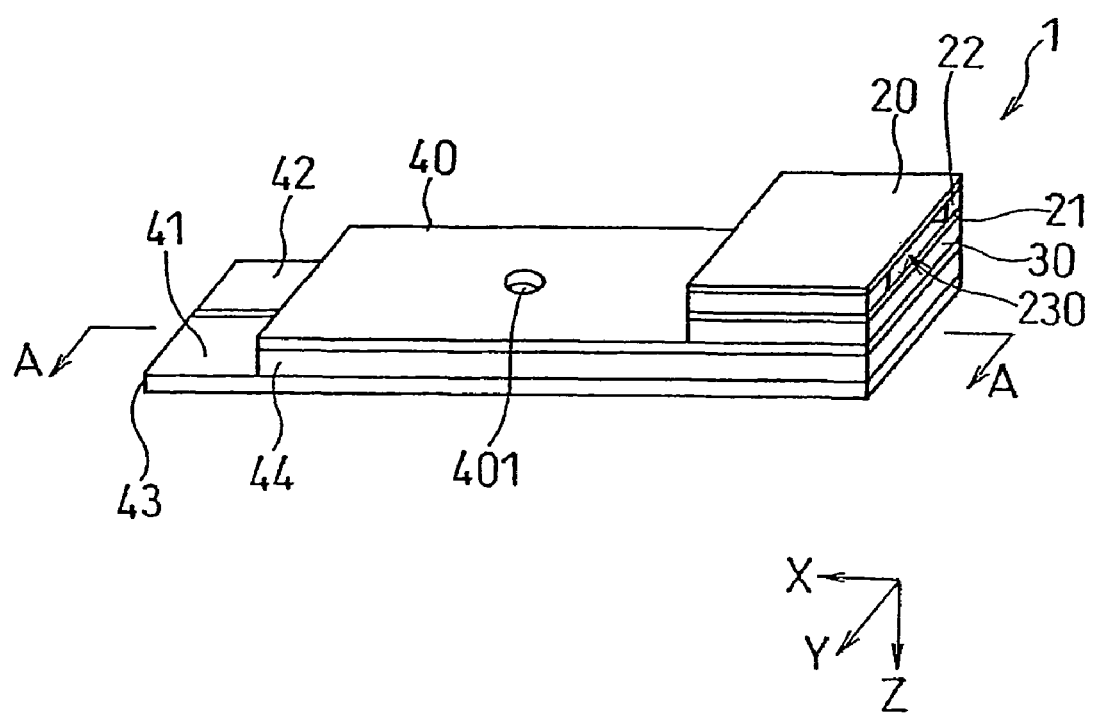
FIG. 2 is a perspective view of the sensor according to one embodiment of the present invention.
Figure 3:
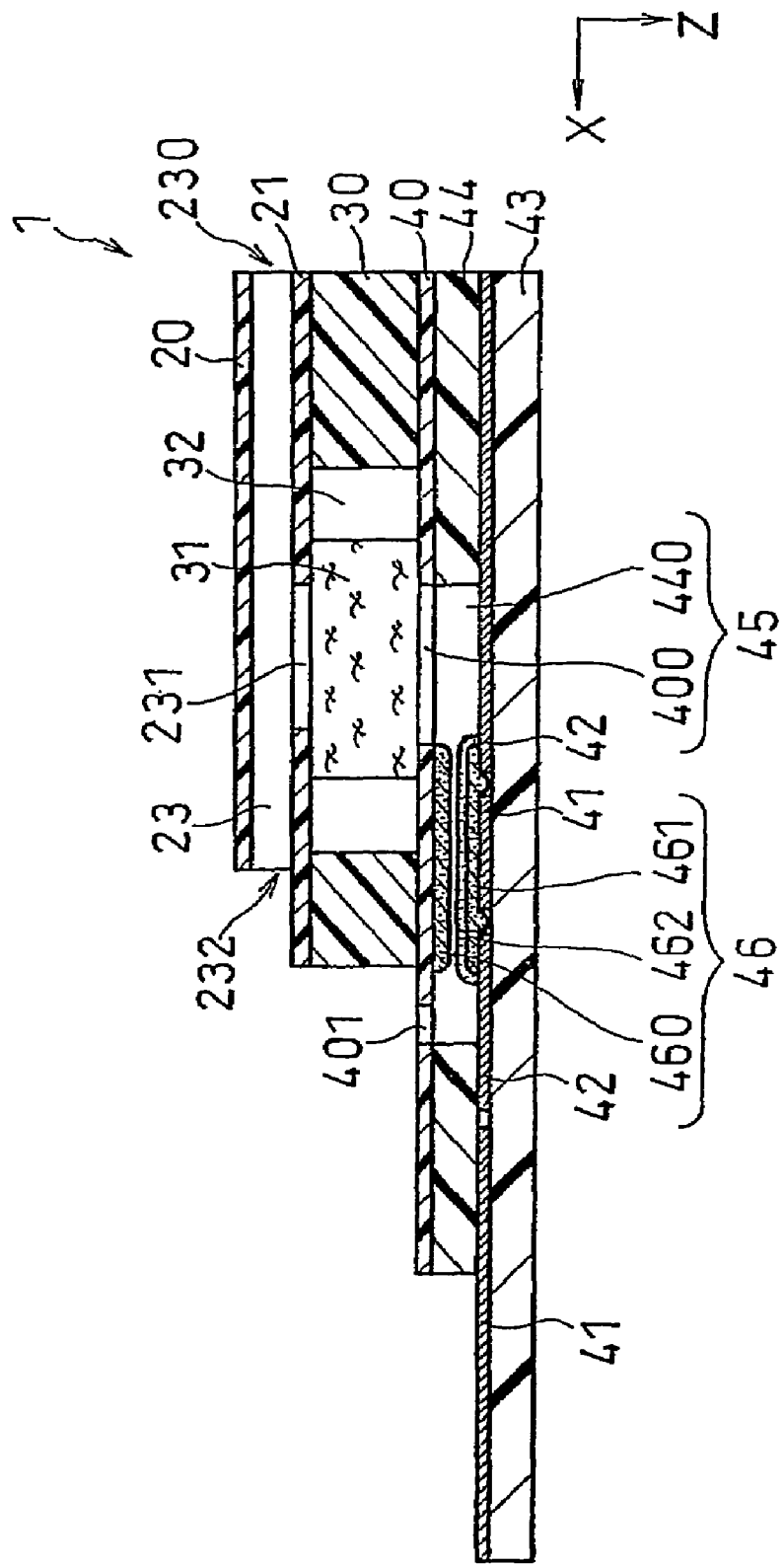
FIG. 3 is a A-A cross-sectional view of the sensor according to one embodiment of the present invention.

The above-described constituent members are stacked in the positional relation as shown by the dash-dotted line of FIG. 1. FIG. 2 shows a perspective view of the sensor 1 obtained by such stacking. Also, FIG. 3 shows an A-A cross-sectional view of the sensor 1. It should be noted that a reagent layer 46 is omitted in FIG. 1.

As illustrated in FIG. 3, the reagent layer 46 is provided in the liquid sample supply path 440. The reagent layer 46 includes a first reagent layer 460, a second reagent layer 461 and a hydrophilic polymer layer 462 containing a hydrophilic polymer. Also, the first reagent layer 460 contains an oxidoreductase and is formed on the lower face of the reaction part cover 40. The second reagent layer 461 contains an electron mediator and is formed on the electrode system of the base plate 43. Over the second reagent layer 461 is formed the hydrophilic polymer layer 462.

Exemplary oxidoreductases contained in the first reagent layer 460 which may be used herein are cholesterol oxydase or cholesterol dehydrogenase, which is an enzyme catalyzing the oxidation reaction of cholesterol, and cholesterol esterase, which is an enzyme catalyzing the conversion process of cholesterol ester into cholesterol. By using them, it is possible to measure the total cholesterol level in blood plasma.

Since the enzyme reaction of cholesterol esterase proceeds very slowly, it is preferred to add a suitable surfactant. Such a surfactant can be selected from n-octyl-β-D-thioglucoside, polyethylene glycol monododecyl ether, sodium cholate, dodecyl-β-maltoside, sucrose monolaurate, sodium deoxycholate, sodium taurodeoxycholate, N,N-bis(3-D-gluconeamidopropyl)deoxycholeamide, polyoxyethylene(10) octyl phenyl ether, etc.

Exemplary electron mediators contained in the second reagent layer 461 include potassium ferricyanide, p-benzoquinone, phenazine methosulfate, methylene blue, and ferrocene derivatives, and they may be used in combination of two or more of them.

Exemplary hydrophilic polymers forming the hydrophilic polymer layer 462 include hydroxyethyl cellulose, hydroxypropyl cellulose, methyl cellulose, ethyl cellulose, ethylhydroxyethyl cellulose, carboxymethyl cellulose, polyvinyl pyrrolidone, polyvinyl alcohol, polyamino acids such as polylysine, polystyrene sulfonic acid, gelatin and derivative thereof, polyacrylic acid and salts thereof, polymathacrylic acid and salts thereof, starch and derivative thereof, and polymers of maleic anhydride or salts thereof. Among them, carboxymethyl cellulose, hydroxyethyl cellulose, and hydroxypropyl cellulose are preferred.

Figure 4:
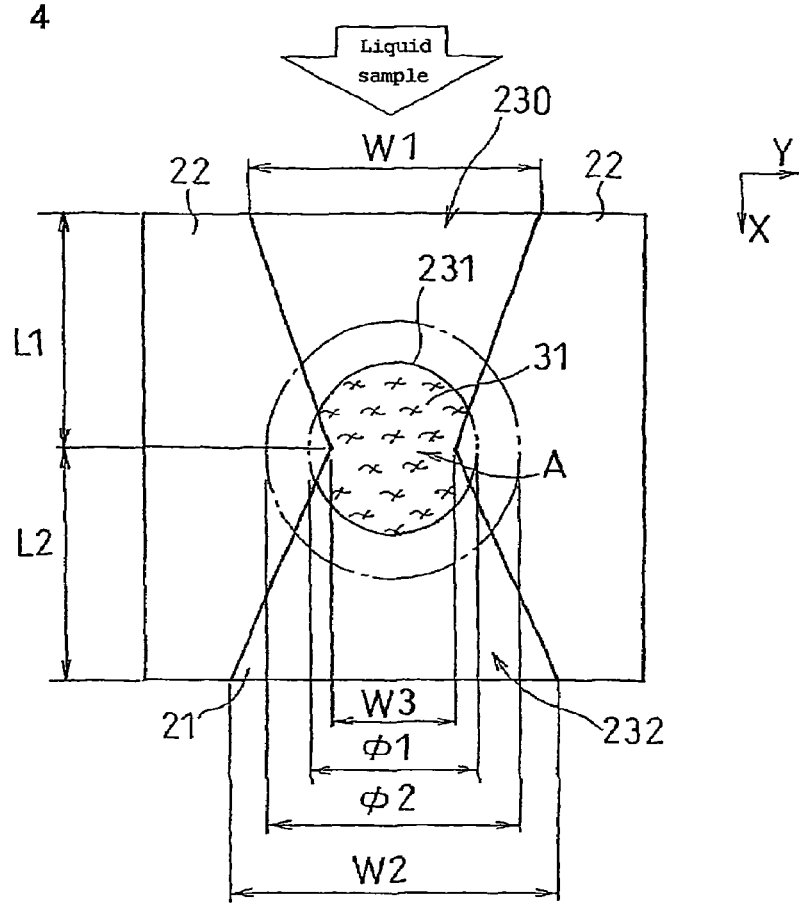
FIG. 4 is a schematic view showing supply means of the sensor according to one embodiment of the present invention.

Detailed description of Shape of Supply Means:

Referring to FIG. 4, the structure of the supply means 2 is described in detail. FIG. 4 is a figure of the supply means 2 of the sensor 1 as illustrated in FIGS. 1 to 3 from which the first cover 20 is removed, which is viewed from above in the direction of the arrow Z. That is, FIG. 4 shows the second cover 21, the two spacers 22, the second opening 231, and the filter 31 seen from the second opening 231.

The supply means 2 has a tunnel structure comprising the space 23 having the first opening 230 and the second opening 231. The first opening 230 and the air vent 232 are located on opposite sides of the supply means 2. And, the two spacers 22, the first cover 20 and the second cover 21 form a capillary space where capillary action is exerted in the region as represented by A of FIG. 4, under which is located the second opening 231 that communicates with the filter. With this structure, a liquid sample supplied from the first opening 230 to the space 23 is sucked in the direction toward the air vent 232, reaching an upper part of the second opening 231. The upper face of the second opening 231 is defined by the second opening 231 and the spacers 22, as will be described below.

The liquid sample having reached the second opening 231 is supplied to the primary surface of the filter 31 through the second opening 231. Such movement wherein the liquid sample supplied to the first opening 230 is sucked into the second opening 231 and then supplied to the filter 31 is mainly subject to capillary action. The structure of the supply means 2 may be any structure that allows capillary action to be exerted in the region A, but it preferably satisfies the following conditions (a) to (c) in order to suck a liquid sample promptly and accurately.

(a) As illustrated in FIG. 4, the space 23 of the supply means 2 is narrowed from the first opening 230 toward the region A. Also, the space 23 of the supply means 2 is narrowed from the air vent 232 toward the region A. That is, the shape of the spacer 22 is preferably designed to be constricted in the middle such that the space 23 narrows from the first opening 230 and the air vent 232 toward the second opening 231. It is preferred that the width W1 of the first opening 230 and the width W2 of the air vent 232 be greater than the smallest inter-wall width W3 in the region A of the space 23. It is also preferred that the center of the second opening 231 be located at the position at which the inter-wall width becomes the smallest. By the above, a liquid sample supplied from the first opening 230 to the space 23 is promptly sucked into the second opening 231.

(b) It is preferred that the distance L1 from the first opening 230 to the center of the upper face of the second opening 231 be equal to or greater than the distance L2 from the air vent 232 to the center of the second opening 231. By this, a liquid sample supplied from the first opening 230 to the space 23 is promptly sucked into the second opening 231.

(c) It is preferred that the largest diameter φ1 of the second opening 231 be equal to or greater than the smallest inter-wall width W3 in the region A of the space 23. Above the second opening 231 is located the region A that is defined by the second opening 231 and the spacers 22. Such structure allows a liquid sample to be promptly supplied to the second opening 231 along the side faces of the walls of the region A, thereby making it possible to prevent the liquid sample from being supplied only to the outer periphery of the second opening 231.

It is also preferred that the largest width φ1 of the second opening 231 be equal to or less than the distance L2 from the center of the second opening 231 to the air vent 232. If this condition is not satisfied, a liquid sample moving toward the second opening 231 by capillary action may escape from the air vent 232 to the outside.

Also, with respect to the second opening 231 and the filter 31, it is preferred that the following conditions (d) and (e) be satisfied.

(d) It is preferred that the area of the second opening 231 be equal to or less than the cross-sectional area of the primary surface of the filter 31. It is preferred to arrange them in such a manner that if the second opening 231 is projected onto the filter 31, the projected portion (opening portion) is included in the filter 31. In this embodiment, the diameter φ1 of the second opening 231 is made equal to or less than the diameter φ2 of the filter 31. Also, the second opening 231 and the filter 31 are arranged such that the center of the second opening 231 and the center of the filter 31 align in the Z axis direction as shown in FIGS. 1 to 3. Such arrangement allows a liquid sample to be reliably supplied to the primary surface of the filter 31. Therefore, a liquid sample is prevented from reaching the reaction part 4 without passing through the filter 31 for filtration.

(e) It is preferred that the shape of the second opening 231 and the sectional shape of the primary surface of the filter 31 are similar to each other. They are circular in this embodiment. By this, a liquid sample is uniformly supplied to the primary surface of the filter 31, so that the filtration function of the filter 31 can be fully utilized.

By combining the above-described conditions (a) to (e), the supply means 2 can promptly and accurately suck and supply a liquid sample to the filter 31 by capillary action. Although the supply means 2 is preferably designed so as to satisfy all of the above conditions (a) to (e), the supply means 2 may be designed so as to satisfy one of these conditions.

Figure 5:
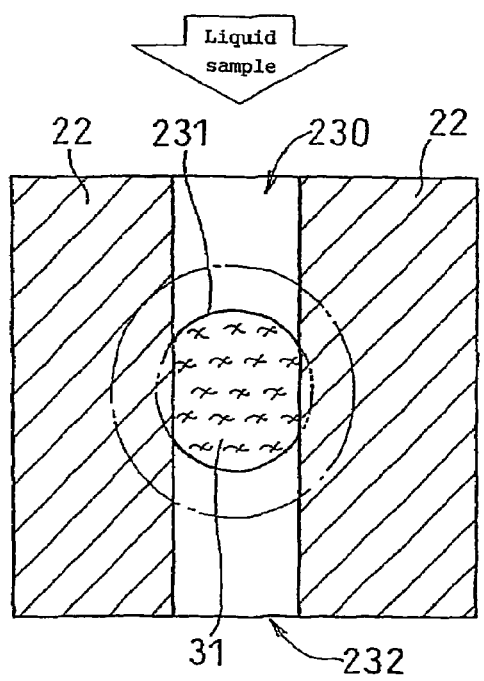
FIG. 5 is a schematic view showing supply means of a sensor according to another embodiment of the present invention.
Figure 6:
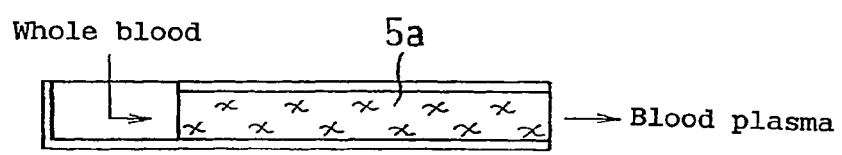
FIG. 6 is a schematic cross-sectional view of a filter that separates blood according to a horizontal separation system.
Figure 7:
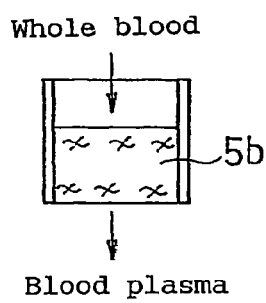
FIG. 7 is a schematic cross-sectional view of a filter that separates blood according to a vertical separation system.
Figure 8:
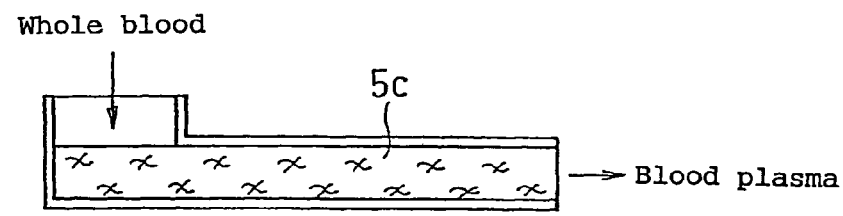
FIG. 8 is a schematic cross-sectional view of a filter that separates blood according to a combined separation system.

For example, as illustrated in FIG. 5, the spacers 22 of the supply means 2 may have the shape of a rectangular prism so as to make the space from the first opening 230 to the air vent 232 have the shape of a rectangular prism. In this case, the above conditions (b) to (e) are satisfied.

By changing the shape of the space of the supply means 2 as described above, the amount of a liquid sample supplied to the filter 31 can be regulated. Also, it is preferred that the volume of the space from the first opening 230 to the second opening 231 be equal to or greater than the total volume of the volume of the gap of the filter 31 and the volume of the space of the reaction part (liquid sample supply path 440).

By forming the supply means 2 as described above, it is possible to regulate the supply speed of a liquid sample to the filter 31, the supply amount thereof, and the dropping position thereof on the primary surface of the filter 31. Accordingly, the filtration function of the filter 31 can be fully utilized, and hemocytes can be promptly and accurately filtered.

Measuring Operations:

An example of measuring cholesterol in blood using the sensor 1 according to the present invention is described with reference to FIG. 3. The user applies blood to the first opening 230. The first opening 230 is located in a side face of the sensor 1. Thus, for example, when collecting blood from a finger, the user only needs to bring the finger into contact with the first opening 230 located in the side face of the sensor 1. Also, according to the present invention, since blood which is a liquid sample is supplied to the filter 31 by capillary action, the sensor 1 does not necessarily need to be held substantially horizontally. Hence, the operability is improved in comparison with conventional cases where blood is directly dropped to the filtration part.

The blood applied to the first opening 230 is sucked into the supply means 2 by capillary action. The blood sucked from the first opening 230 in the direction of the air vent 232 (the substantially horizontal direction relative to the base plate 43) passes through the second opening 231, permeates through the filter 31 from the primary surface of the filter 31, and is filtered in the direction substantially vertical to the base plate 43.

Inside the filter 31, the permeation speed of hemocytes is slower than the permeation speed of blood plasma, which is a liquid component. Thus, while the hemocytes remain in the filter 31, the blood plasma oozes from the secondary surface of the filter. The blood plasma having oozed therefrom is supplied to the liquid sample supply path 440. This blood plasma is sucked by capillary action from the connection hole 400 in the direction of the second air vent 401 and fills the liquid sample supply path 440 while dissolving the reagent layer 46. In this state, the flow of the blood stops.

The blood plasma and reagents chemically react as follows. Specifically, with the cholesterol esterase contained in the first reagent layer 460 as the catalyst, cholesterol ester in the blood plasma changes into cholesterol. This reaction proceeds promptly due to the surfactant contained in the first reagent layer 460. And, this cholesterol and the cholesterol originally contained in the blood plasma change into cholestenone, with the cholesterol oxidase or cholesterol dehydrogenase contained in the first reagent layer 460 as the catalyst. At this time, the electron mediator contained in the second reagent layer 461 is reduced. For example, when potassium ferricyanide is used as the electron mediator, this potassium ferricyanide is reduced to potassium ferrocyanide.

After the lapse of a predetermined period of time, using a measuring device, a voltage is applied between the working electrode 41 and the counter electrode 42, to electrochemically oxidize this electron mediator. By measuring the current value at this time, the cholesterol in the blood can be quantified.

By providing the supply means 2 as described above, the filtration function of the filter 31 can be fully exhibited, and blood is promptly and accurately filtered. Thus, hemocytes remain within the filter 31 and only blood plasma is supplied to the liquid sample supply path 440. That is, hemocytes can be prevented from entering the liquid sample supply path 440. It is therefore possible to prevent the destruction of hemocytes by the surfactant contained in the first reagent layer 460 and hence the adverse effect of reducing substances contained in the hemocytes, such as glutathione, upon the reaction. Accordingly, the measurement accuracy and the simultaneous reproducibility are improved.

Others:

The sensor according to the present invention is not to be limited to the sensor 1 as described in the foregoing embodiments. It may have any structure as long as a liquid sample is supplied by supply means to a filtration part for filtration and is then supplied to a reaction part having reagents that react with the liquid sample that has been filtered at the filtration part. Other structural requirements are described below.

The positional relation between the supply means, the filtration part, and the reaction part can be changed where appropriate. For example, with respect to the filtration system, the vertical separation system is preferable since it has the following and other advantages: due to the utilization of gravity for filtration, the filtration distance is short and prompt filtration is therefore possible; since the filter does not enter the liquid sample supply path, the effect of the filter on the reaction system is small. However, filtration systems such as the horizontal separation system and the combined separation system may be employed if the positional relation between the supply means, the filtration part, and the reaction part is changed.

The structure of the supply means may be any structure as long as a liquid sample can be sucked to the filtration part by capillary action. For example, the air vent may be provided in the filtration part without being provided in the supply means.

The filtration part is sufficient if it has the function of filtering a liquid sample. In the case of using the filter, one filter may be used, or two or more filters may be used. The shape and material of the filter is also adjustable to the degree that the filtration function is not degraded.

With respect to the reagents in the reaction part, by selecting an appropriate oxidoreductase depending on the substance to be measured, it is also possible to measure blood sugar level, lactic acid level, etc., as well as cholesterol. Exemplary oxidoreductases that can be used include glucose oxydase, fructose dehydrogenase, glucose dehydrogenase, alcohol oxydase, lactic acid oxydase, cholesterol oxydase, cholesterol esterase, xanthine oxydase, and amino acid oxydase.

Although the electrode system of the reaction part has been described as a two-electrode system in the foregoing embodiments, it may be a three-electrode system that further includes a reference electrode. Generally, the three-electrode system enables more accurate measurements than the two-electrode system. Further, an optical method, not an electrochemical method, may be used to quantify or detect a measuring substance in the reaction part. For example, as a reagent, a colorant that changes color through enzyme reaction may be used. By optically measuring the change in the color of the colorant, the content of a measuring substance may be quantified.

INDUSTRIAL APPLICABILITY

Although the foregoing embodiments have been described by referring to an instance where the liquid sample is blood and the substance to be measured is a component of blood plasma, the present invention is not to be limited to only those. Also, the measuring target is not to be limited to body fluid components such as blood, and the sensor in accordance with the present invention is applicable, for example, to measuring devices that measure on the spot the quality of water in lakes and marshes which is turbid due to microorganisms, dead bodies thereof, sludge, etc.

For example, a sensor having only the supply means 2 and the filtration part 3 of FIG. 1 is produced and an adhesive is applied to the bottom of the spacer 30 of the filtration part. Then, this sensor can be affixed to the measuring part of a commercially available portable measuring device (e.g., pH meter such as model B-211 manufactured by Horiba, Ltd.) when used. In this case, by bringing the above-mentioned supply means and filtration part into contact with turbid water of a lake or marsh, this water can be sucked and filtered as the liquid sample, and the filtered liquid sample can be supplied to the measuring part of the measuring device (e.g., electrode).

The sensor in accordance with the present invention can supply a suitable amount of a liquid sample to a filter promptly and readily.

The invention claimed is:

1. A sensor comprising:
a reaction part, a filtration part, and a supply means, wherein,
said reaction part, said filtration part, and said supply means are stacked in this order,
said supply means being provided for supplying a liquid sample to said filtration part by capillary action,
said filtration part including a filter for supplying a filtered liquid sample to said reaction part,
said reaction part having a reagent that reacts with said liquid sample that has been filtered in said filter,
said reaction part including a base plate and a plate-like reaction part spacer that are stacked in order,
said plate-like reaction part spacer having a cavity inside, said cavity provided with said reagent, said supply means including a plate-like bottom cover, plate-like spacers, and a plate-like top cover that are stacked in order, said plate-like spacers providing a space inside, said plate-like spacers providing at the side faces thereof a first opening and an air vent, each facing to the direction parallel to the surface of said base plate;

said plate-like bottom cover having a second opening, said space and said second opening being communicated, the width of said space narrows in the direction from said first opening toward said second opening, seen in planar view, or, the width of said space from said first opening until said second opening is fixed, seen in planar view, so that said liquid sample that is injected from said first opening is directed toward said second opening by capillary action.

2. The sensor in accordance with claim 1, wherein the width of said space narrows from said first opening toward said second opening, seen in planar view.

3. The sensor in accordance with claim 2, wherein the width of said space narrows from said air vent toward said second opening, seen in planar view.

4. The sensor in accordance with claim 1, wherein the width of said space from said first opening until said second opening is fixed, seen in planar view.

5. The sensor in accordance with claim 1, wherein the cross-sectional area of said second opening is smaller than the cross-sectional area of said filter.

6. The sensor in accordance with claim 5, wherein the cross-section of said second opening is similar to the cross-section of said filter.

7. The sensor in accordance with claim 6, wherein the volume of said space from said first opening to said second opening is equal to or larger than the total volume of the volume of a gap around said filter and the volume of a space inside said reaction part.

8. The sensor in accordance with claim 1, wherein said reaction part has a second air vent.

* * * * *